(12) United States Patent
Scott et al.

(10) Patent No.: US 9,594,007 B2
(45) Date of Patent: Mar. 14, 2017

(54) CHROMATOGRAPHY APPARATUS AND METHOD

(71) Applicant: EMD Millipore Corporation, Billerica, MA (US)

(72) Inventors: Chris Scott, Westford, MA (US); Rob Colonna, Boston, MA (US); Christopher Barmore, Arlington, MA (US); Todd Taylor, Marlborough, MA (US); Daniel Morgan, Hampton, NH (US)

(73) Assignee: EMD Millipore Corporation, Billerica, MA (US)

( * ) Notice: Subject to any disclaimer, the term of this patent is extended or adjusted under 35 U.S.C. 154(b) by 288 days.

(21) Appl. No.: 14/309,051

(22) Filed: Jun. 19, 2014

(65) Prior Publication Data

US 2014/0298924 A1    Oct. 9, 2014

Related U.S. Application Data

(63) Continuation of application No. 13/311,597, filed on Dec. 6, 2011, now Pat. No. 9,157,838.
(Continued)

(51) Int. Cl.
*G01N 1/28* (2006.01)
*G01N 1/40* (2006.01)
(Continued)

(52) U.S. Cl.
CPC .............. *G01N 1/28* (2013.01); *B01J 20/281* (2013.01); *G01N 1/4077* (2013.01); *G01N 30/14* (2013.01);
(Continued)

(58) Field of Classification Search
CPC ....................................................... G01N 1/28
See application file for complete search history.

(56) References Cited

U.S. PATENT DOCUMENTS

D263,078 S   2/1982  Eddleman et al.
4,444,661 A  4/1984  Jackson et al.
(Continued)

FOREIGN PATENT DOCUMENTS

WO   03/049831 A2   6/2003
WO   2004/101151 A1  11/2004

OTHER PUBLICATIONS

Office action mailed Oct. 21, 2015 in co-pending U.S. Appl. No. 14/109,988.
(Continued)

*Primary Examiner* — Hezron E Williams
*Assistant Examiner* — David Z Huang
(74) *Attorney, Agent, or Firm* — Nields, Lemack & Frame, LLC

(57) ABSTRACT

Sample preparation device for receiving in sealing relation one or more filter assemblies and one or more sample containers, each container uniquely positioned within the device to receive filtered sample from a designated filter. The device includes a body, a lid disposed on the body, a container tray, a base, an integrated seal on the body, a valve and a valve actuator. The tray can be disposed in a vacuum chamber defined by the lid and the body, and one or more sample containers can be disposed in the tray. When properly positioned in the tray in the vacuum chamber, each container is in fluid communication with a single respective filter assembly disposed in sealing relation in a respective aperture in the lid. A single actuation of a valve to place the
(Continued)

vacuum chamber under vacuum causes the lid to seal to the base and drives the simultaneous filtration of a plurality of samples.

14 Claims, 27 Drawing Sheets

Related U.S. Application Data

(60) Provisional application No. 61/426,849, filed on Dec. 23, 2010.

(51) Int. Cl.
| | | |
|---|---|---|
| *G01N 30/14* | (2006.01) | |
| *B01J 20/281* | (2006.01) | |
| B01D 61/18 | (2006.01) | |
| B01L 3/00 | (2006.01) | |

(52) U.S. Cl.
CPC ........... *B01D 61/18* (2013.01); *B01L 3/50255* (2013.01); *G01N 2030/146* (2013.01)

(56) References Cited

U.S. PATENT DOCUMENTS

| | | | |
|---|---|---|---|
| D285,487 S | 9/1986 | Tjernagel | |
| 4,810,471 A | 3/1989 | Wachob et al. | |
| 4,948,442 A | 8/1990 | Manns | |
| 4,948,564 A | 8/1990 | Root et al. | |
| 5,141,719 A | 8/1992 | Fernwood et al. | |
| 5,223,133 A | 6/1993 | Clark et al. | |
| 5,230,727 A | 7/1993 | Pound et al. | |
| 5,264,184 A | 11/1993 | Aysta et al. | |
| 5,342,581 A | 8/1994 | Sanadi | |
| 5,620,663 A | 4/1997 | Aysta et al. | |
| 5,648,271 A | 7/1997 | Kempe | |
| 6,058,676 A * | 5/2000 | Abraham | B25B 11/005 53/287 |
| 6,131,573 A | 10/2000 | Brown | |
| D441,449 S | 5/2001 | Gaskell | |
| 6,338,802 B1 | 1/2002 | Bodner et al. | |
| 6,419,827 B1 | 7/2002 | Sandell et al. | |
| 6,627,072 B1 | 9/2003 | Ridge | |
| 6,864,100 B1 | 3/2005 | Ribbe et al. | |
| 6,878,343 B2 | 4/2005 | Sklar et al. | |
| 6,966,443 B1 | 11/2005 | Ridge | |
| 7,135,117 B2 | 11/2006 | Kane | |
| D535,750 S | 1/2007 | Clawson | |
| D569,685 S | 5/2008 | Liu | |
| 7,588,728 B2 | 9/2009 | Clark et al. | |
| RE42,231 E | 3/2011 | Spurgeon | |
| D679,812 S | 4/2013 | Taylor et al. | |
| D681,816 S | 5/2013 | Taylor et al. | |
| 9,157,838 B2 | 10/2015 | Scott et al. | |
| 2002/0150505 A1 | 10/2002 | Reed et al. | |
| 2003/0057148 A1 | 3/2003 | Zuk, Jr. | |
| 2004/0005608 A1 | 1/2004 | Saghbini et al. | |
| 2005/0019775 A1 | 1/2005 | Alderborn et al. | |
| 2005/0051471 A1 | 3/2005 | Lane et al. | |
| 2005/0058577 A1 | 3/2005 | Micklash, II et al. | |
| 2005/0130196 A1 | 6/2005 | Hofstadler et al. | |
| 2005/0178216 A1 | 8/2005 | Pitt et al. | |
| 2012/0297899 A1 | 11/2012 | Scott et al. | |
| 2014/0105795 A1 | 4/2014 | Scott et al. | |

OTHER PUBLICATIONS

Final Rejection mailed Mar. 27, 2015 in corresponding parent U.S. Appl. No. 13/311,597.
Pall Life Sciences, May 2003, AcroPrep 24 Filtration System Product Information, 4 pages.
International Search Report/Written Opinion mailed Apr. 19, 2012 in corresponding PCT application No. PCT/US 11/63644.
International Preliminary Report on Patentability mailed Jul. 4, 2013 in corresponding PCT application No. PCT/US11/63644.
Office Action—Restriction—mailed Dec. 4, 2013 in corresponding U.S. Appl. No. 13/311,597.
Office Action mailed Jan. 14, 2014 in corresponding U.S. Appl. No. 13/311,597.
Final Rejection mailed May 12, 2014 in corresponding U.S. Appl. No. 13/311,597.
Final Rejection mailed Jul. 14, 2014 in corresponding U.S. Appl. No. 13/311,597.
Notice of Allowance mailed Jul. 13, 2015 in corresponding parent U.S. Appl. No. 13/311,597.
Office Action mailed Nov. 4, 2014 in corresponding parent U.S. Appl. No. 13/311,597.
Notice of Allowance mailed May 5, 2016 in co-pending U.S. Appl. No. 14/109,988.

* cited by examiner

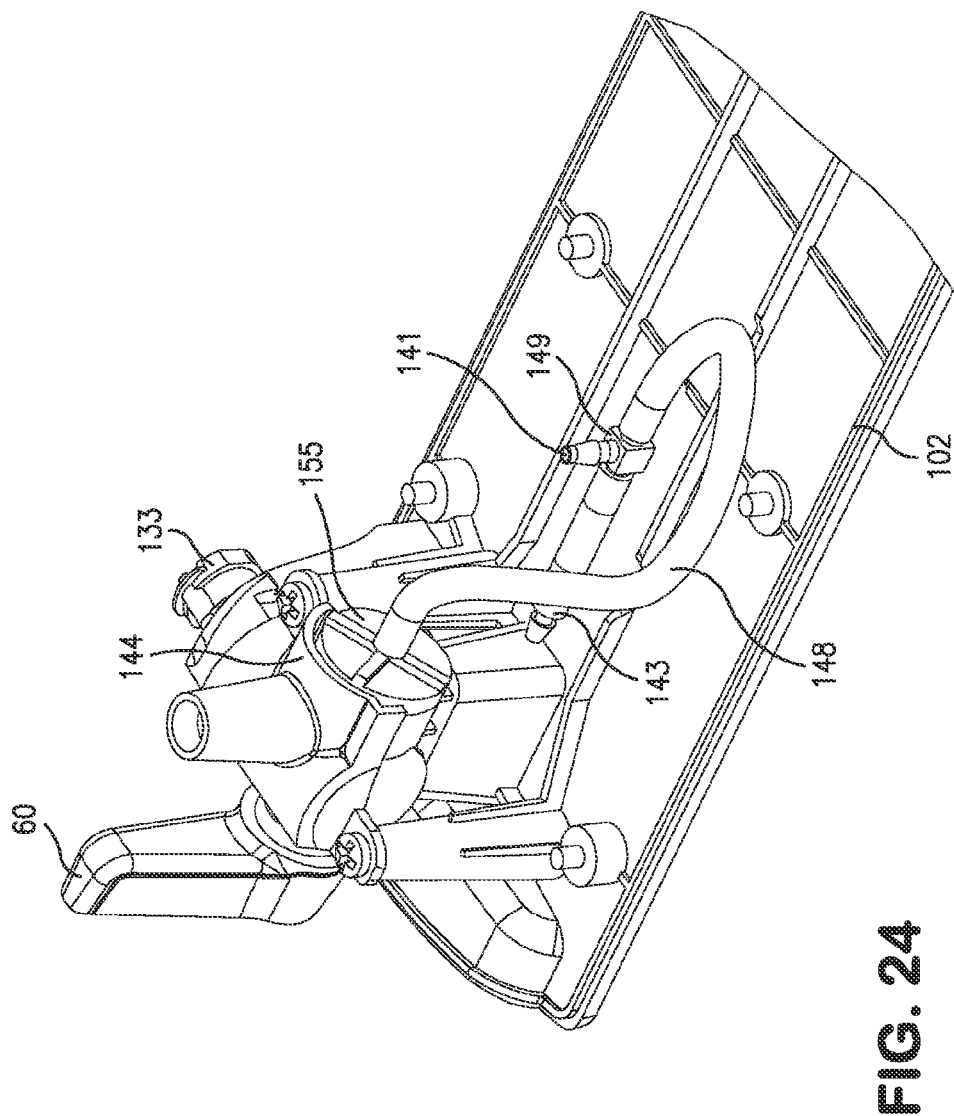

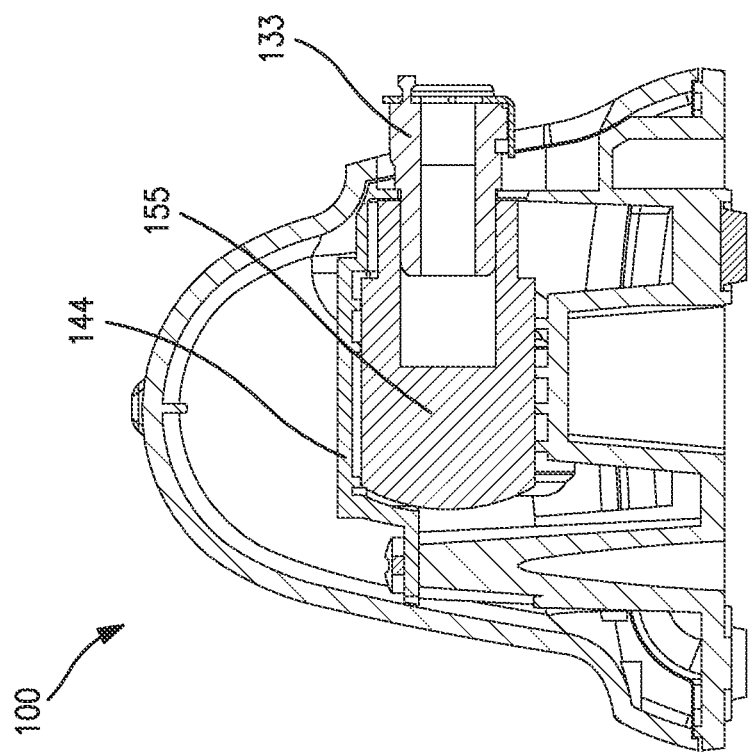

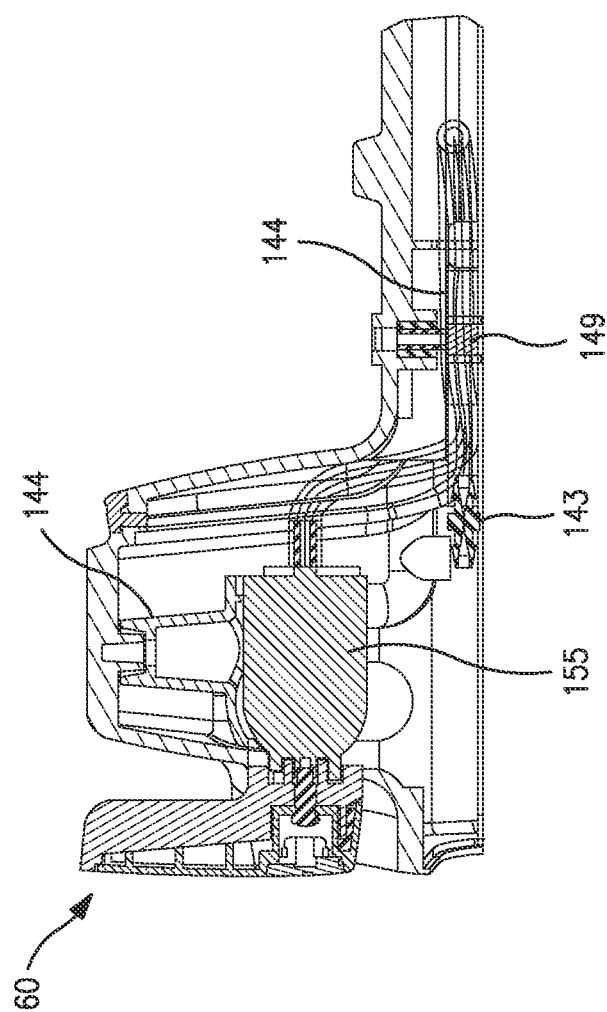

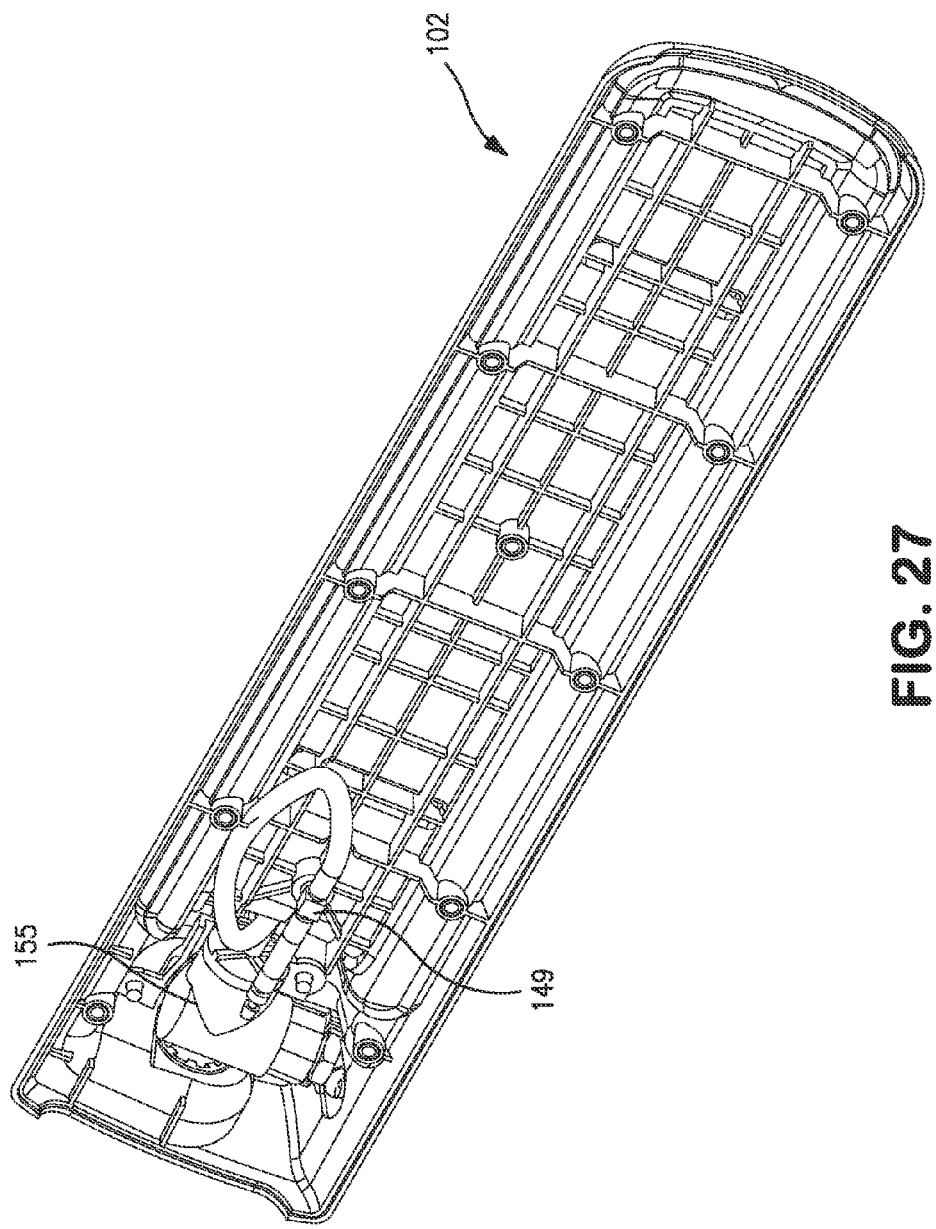

CHROMATOGRAPHY APPARATUS AND METHOD

This application is a continuation of U.S. patent application Ser. No. 13/311,597 filed Dec. 6, 2011, which claims priority of U.S. Provisional Application Ser. No. 61/426,849 filed Dec. 23, 2010, the disclosures of which are incorporated herein by reference.

BACKGROUND

To satisfy researchers' demands for more information about their compounds of interest, manufacturers of HPLC, UHPLC, LC/MS and GC/MS systems are constantly developing new technologies that lower the detection limits of these separation systems. Accompanying these ever decreasing detection limits is the need for higher purity samples and cleaner mobile phases. Samples and buffers, after proper filtration, not only generate higher quality, more consistent results, they also increase instrument. uptime and prolong column life.

One conventional sample preparation device for chromatography applications is a Millex® filter, commercially available from Millipore Corporation. These filters are non-sterile, low-extractable filters for clarification or fine particulate removal prior to instrument analysis. Millex® filter units contain a membrane in a housing, such as a high density polyethylene or polypropylene housing. One or more filter layers are permanently sealed between two plastic filter holder halves, the first half having an inlet port and the second half having an outlet port. The outer peripheral edge of the membrane is trapped between the two halves. The outer peripheral edges and of the two halves can be sealed together by an overmold of plastic to form a liquid tightly sealed device. A variety of membranes and housings ensure chemical compatibility with a range of samples and solvents. For example, Millex®-LCR filters contain a hydrophilic PTFE membrane and are HPLC-certified for low levels of UV-absorbing extractables, and provide a very clean sample for HPLC analysis. Durapore® (PVDF) filters combine fast flow with low protein binding. Nylon filters provide broad chemical compatibility for use with aqueous and organic solutions. Millipore Express® PLUS (PES) filters have high flow rates and higher throughput. MF-Millipore™ mixed cellulose ester (MCE) membrane is a widely used, general purpose filter. Glass fiber can be used for clarifying aqueous or organic solutions with high particulate levels and can also be present in the housing as a prefilter. Depending on process volume, filter sizes range from 4 mm to 33 mm in diameter. The Millex® filters are used in conjunction with pressure driven hand-held syringes.

It would be desirable to increase the speed and ease the preparation of one or more samples for applications such as HPLC analysis, while reducing the occurrence of human error, the repetitive motion and duration of the applied load necessary to operate hand-held devices, and the presence of contaminants.

SUMMARY

The embodiments disclosed herein provide an alternative to time-consuming one-at-a-time syringe filters. A driving force such as vacuum is used to drive filtration and process a single sample, or multiple samples simultaneously and in parallel. In certain embodiments, one or a plurality of disposable filters, each having an integrated funnel and seal, is used in conjunction with a manifold, to filter one or a plurality of samples into respective sample containers such as vials that are in liquid-receiving communication with a respective filter. In certain embodiments, the disposable filter is packaged in groups of four, which can be selectively separated from each other. The filter assembly design achieves a hold up volume of less than 100 µl. As a result, smaller starting sample volumes can be used than is the case with syringes.

In accordance with certain embodiments, a sample preparation device comprises a device body, wherein the device is adapted to receive in sealing relation one or more filter assemblies. The device is also adapted to receive one or more sample containers such as vials. Each vial is uniquely positioned within the device to receive filtered sample from a designated filter. In certain embodiments, the device includes a body, including a base, a removable clear lid disposed on said base in sealing relation, a removable vial tray, an integrated seal on the base, a valve and a valve actuator. The removable vial tray can be disposed in a vacuum chamber defined by the lid and the base, and one or more vials can be removably disposed in the vial tray. When properly positioned in the vial tray in the vacuum chamber, each vial is in fluid communication with a single respective filter assembly disposed in sealing relation in a respective aperture in the lid. In certain embodiments, the assembly has an interior region that is in fluid communication with a vacuum source. Application of vacuum from the vacuum source causes the lid to seal to the base, and drives filtration. A single actuation of a valve to place the vacuum chamber under vacuum causes the simultaneous filtration of a sample or a plurality of samples.

BRIEF DESCRIPTION OF THE DRAWINGS

FIG. 24 is a perspective view of a valve assembly for placing a vacuum chamber in and out of fluid communication with a vacuum source, in accordance with certain embodiments;

FIG. 25 is a cross-sectional view of a valve in a sample preparation device in accordance with certain embodiments;

FIG. 26 is a partial cross-sectional view of the valve assembly of FIG. 24 in accordance with certain embodiments; and FIG. 27 is a bottom perspective view of the valve assembly of FIG. 24 in accordance with certain embodiments.

DETAILED DESCRIPTION

Figure 1:
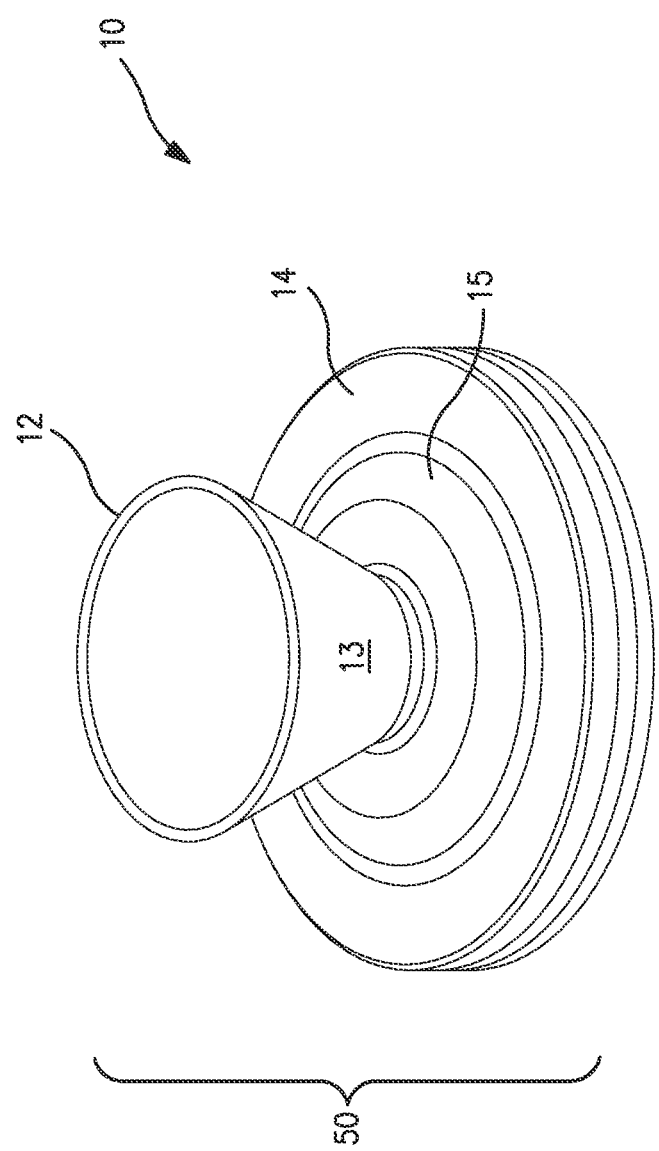
FIG. 1 is a top perspective view of a filter assembly in accordance with certain embodiments.
Figure 2:
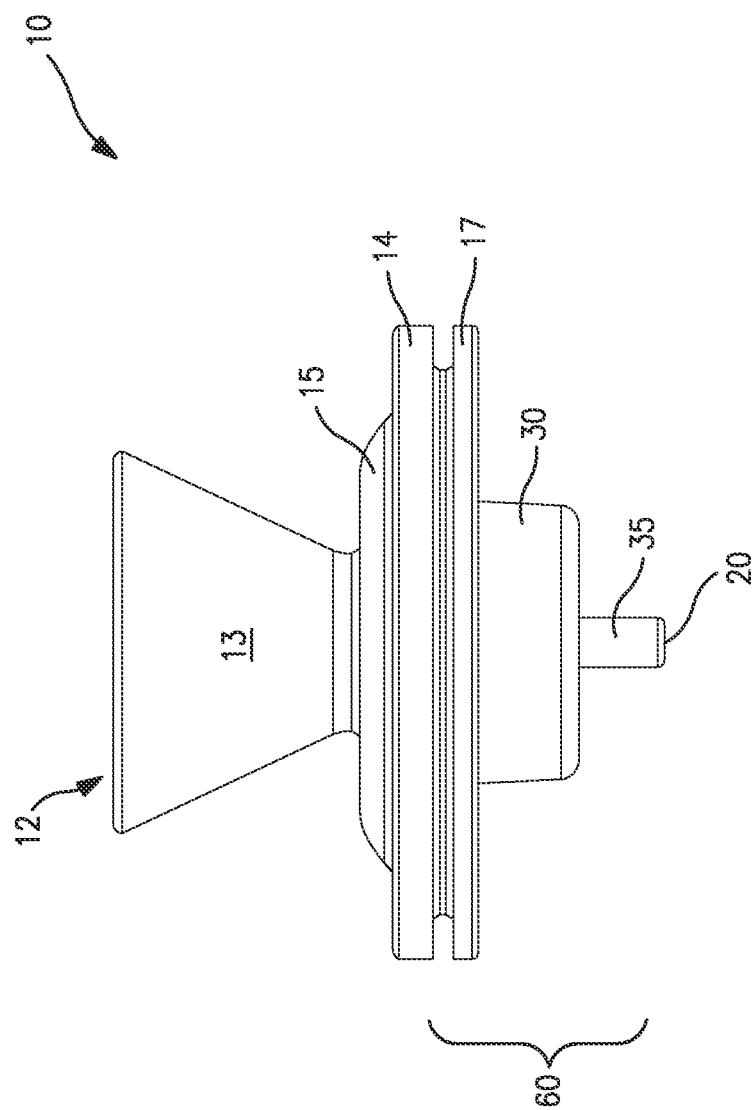
FIG. 2 is a side view of the filter assembly of FIG. 1.
Figure 3:
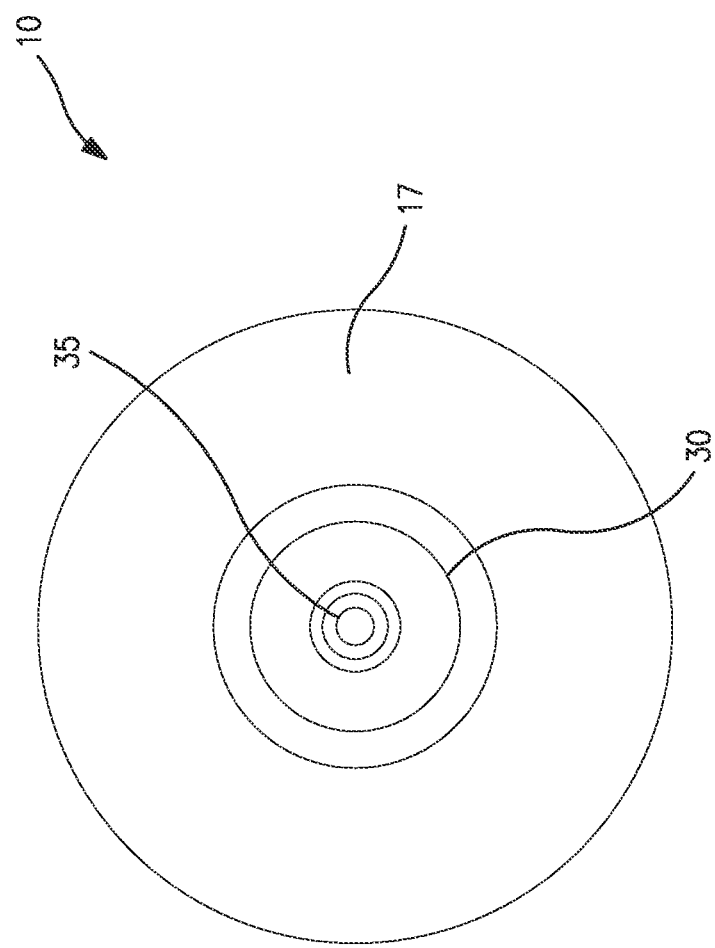
FIG. 3 is a bottom view of the filter assembly of FIG. 1.
Figure 4:
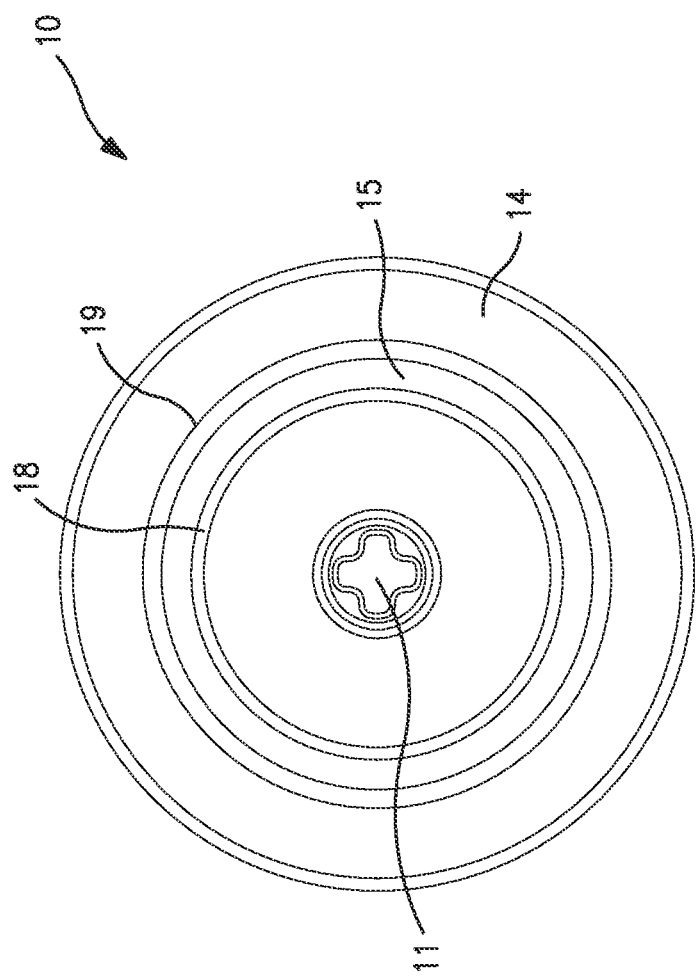
FIG. 4 is a top view of the upper housing unit of the filter assembly of FIG. 1.
Figure 5:
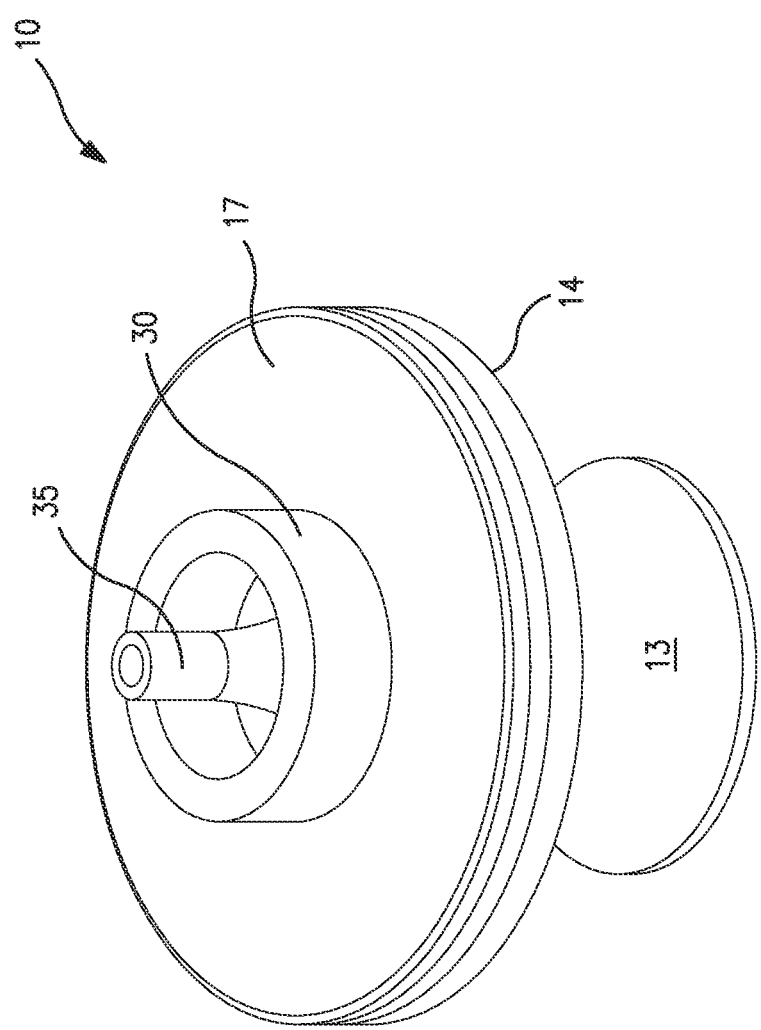
FIG. 5 is a bottom perspective view of the filter assembly of FIG. 1.
Figure 6:
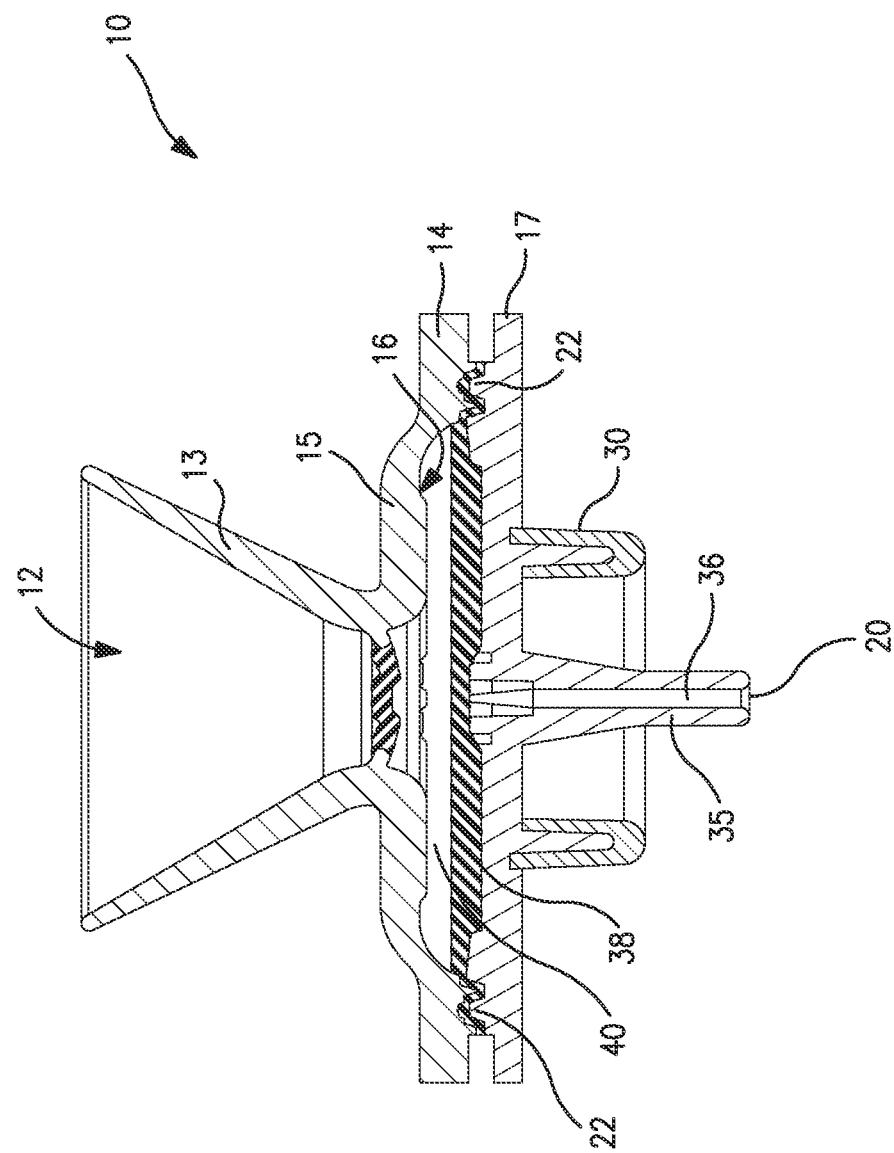
FIG. 6 is a cross-sectional view of the filter assembly of FIG. 1.

Turning to FIGS. 1-6, there is shown a filter assembly 10 particularly suited for use with the sample preparation device in accordance with certain embodiments disclosed herein. The filter assembly 10 includes a sample reservoir 12. The reservoir 12 is of sufficient volume to hold a typical sample desired to be processed. Suitable sample reservoir 12 volumes include 0.5-2.0 ml, although other reservoir volumes are within the scope of the embodiments disclosed herein. In accordance with certain embodiments, the sample reservoir 12 is defined by a fluid impervious wall 13, which is preferably funnel-shaped such that it tapers inwardly from the open inlet towards the filter compartment with which it is in fluid communication via aperture 11. In certain embodiments, the aperture 11 is clover-shaped as best seen in FIG. 4. The funnel-shaped reservoir facilitates filling the reservoir with sample and minimizes the possibility of sample loss during filling. Although a funnel-shape is preferred, other shapes such as cylindrical and cubical, are within the scope of the embodiments disclosed herein. In accordance with certain embodiments, the sample reservoir 12 includes an integrally mounted base 14, the reservoir 12 and base 14 together forming a unitary structure and defining an upper housing unit 50 that can be formed by injection molding. The base is preferably disk-shaped, and optionally can include a raised dome 15 smaller in diameter than the base 14 and defining a prefilter chamber 16 (FIG. 6). Preferably the upper housing unit 50 is made from an inexpensive plastic material so that it can be disposable after a single use, and is made from a material that is injection moldable. A preferred material is high density polyethylene with 1-3% titanium dioxide.

Figure 13:
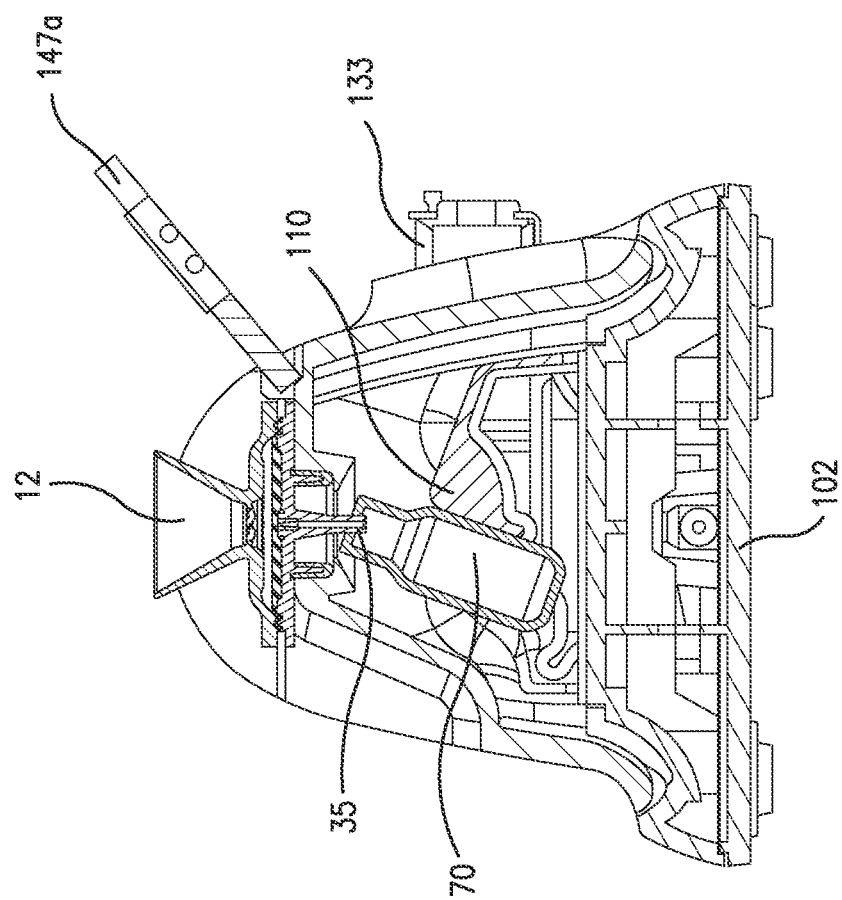
FIG. 13 is an end view, in cross-section, of the device including a filter assembly and vial shown in place, accordance with certain embodiments.
Figure 15:
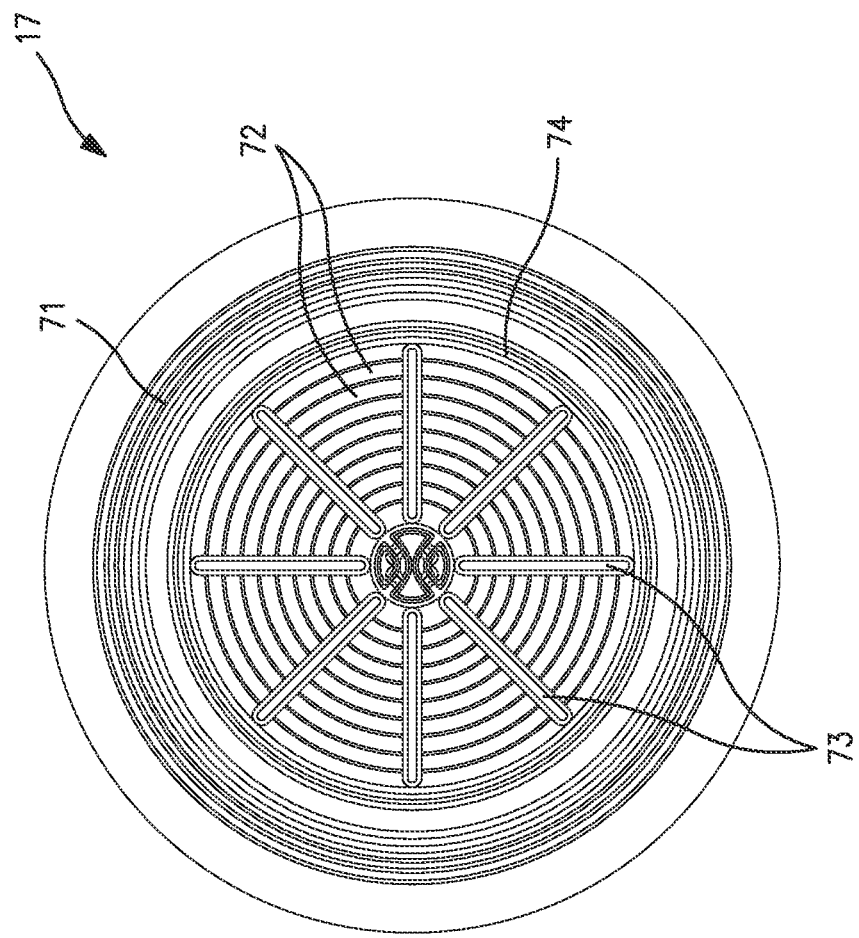
FIG. 15 is a top view of membrane support features in the bottom housing of the filter in accordance with certain embodiments.

The upper housing unit 50 is mounted to a lower housing unit 60, which also can be formed by injection molding. Heat sealing such as by ultrasonic welding can be used to affix the upper and lower units together. To that end, the underside of the base 14 can have concentric raised annular rings 18 and 19 (FIG. 4) which receive between them a raised annular ring 22 (FIG. 6) in the lower housing unit 60, creating a strong bond upon the application of heat. Lower housing unit 60 includes a membrane support member 17. Preferably the membrane support member 17 is made from an inexpensive plastic material so that it can be disposable after a single use, and is made from a material that is injection moldable, such as polyolefins, particularly polyethylene. A preferred material is high density polyethylene, as it exhibits its low extractables and laser print graphics can be used with it. As seen in FIG. 15, the membrane support member 17 includes one or more openings, such as a plurality of concentric circumferential slits 72, which form an underdrain and allow fluid communication between the inlet of the sample chamber 12 and the outlet 20. A plurality of spokes 73, preferably equally spaced, traverse the slits 72 and help support the membrane. An annular heat seal bead 74 can be provided to seal the membrane to the support. An annular ultrasonic weld energy director 71 also can be provided for welding the support to the upper housing unit. The support member 17 is preferably disk-shaped and corresponds in size to the upper housing unit base 14. Lower housing unit 60 includes an axially extending collar member 30 positioned radially inwardly from the outer circumference of the support member 17. The collar member 30 is preferably overmolded on the support member 17, and is made of a thermoplastic elastomer, such as Teknor Apex Monprene® MP 2551B. The collar member 30 is configured to engage with an aperture in the sample preparation device in sealing relation, thereby sealing the filter assembly to the manifold. Preferably the collar member 30 is an annular ring, best seen in FIGS. 5 and 6, having a center along the axial centerline of the membrane support member 17. Also extending axially from the membrane support member 17 is an elongated tip 35, preferably along the axial centerline of the membrane support member 17. The elongated tip 35 includes a bore 36 in fluid communication with the volume 40 defined between base 14 and support member 17 when the upper and lower housing units are in the assembled condition, as shown in FIG. 6. The bore, which is preferably centrally located in the elongated tip 35, terminates in outlet 20. It is preferably of sufficient length that it penetrates into a container 70 (e.g., a standard HPLC vial) positioned in the vacuum chamber operation of the device, as best seen in FIG. 13.

Porous media such as a membrane 38 (FIG. 6) is positioned on the membrane support member 17 and is sealed thereto, such as with the aid of the heat seal bead 74, so that all fluid flow from the inlet 12 through the outlet 20 proceeds through the membrane 38 and does not bypass the same. The characteristics of the membrane will depend upon the sample being processed. Suitable membranes include 0.2 μm PTFE membranes and 0.45 μm hydrophilized PTFE membranes. Where a prefilter is desired, it can be positioned in chamber 16 and may include any suitable prefilter for the application, such as one or more layers of glass fiber.

Each filter assembly 10 containing just the membrane has a sample hold up volume of about 100 μl, whereas conventional syringe filter devices containing the same type of membrane have a hold up volume of about 300-400 μl. Similarly, each filter assembly 10 containing a membrane and a prefilter have a sample hold up volume of about 300 μl, whereas conventional syringe filter devices containing the same combination of membrane and prefilter have a sample hold up volume of about 900-1000 μl. The benefit of low hold up volume for down-stream HPLC applications is that lower sample volume can be used while still obtaining enough sample for HPLC analysis. With low sample hold up, less sample is lost to the filter, thereby allowing researchers to use their sample for more tests following filtration.

Figure 7:
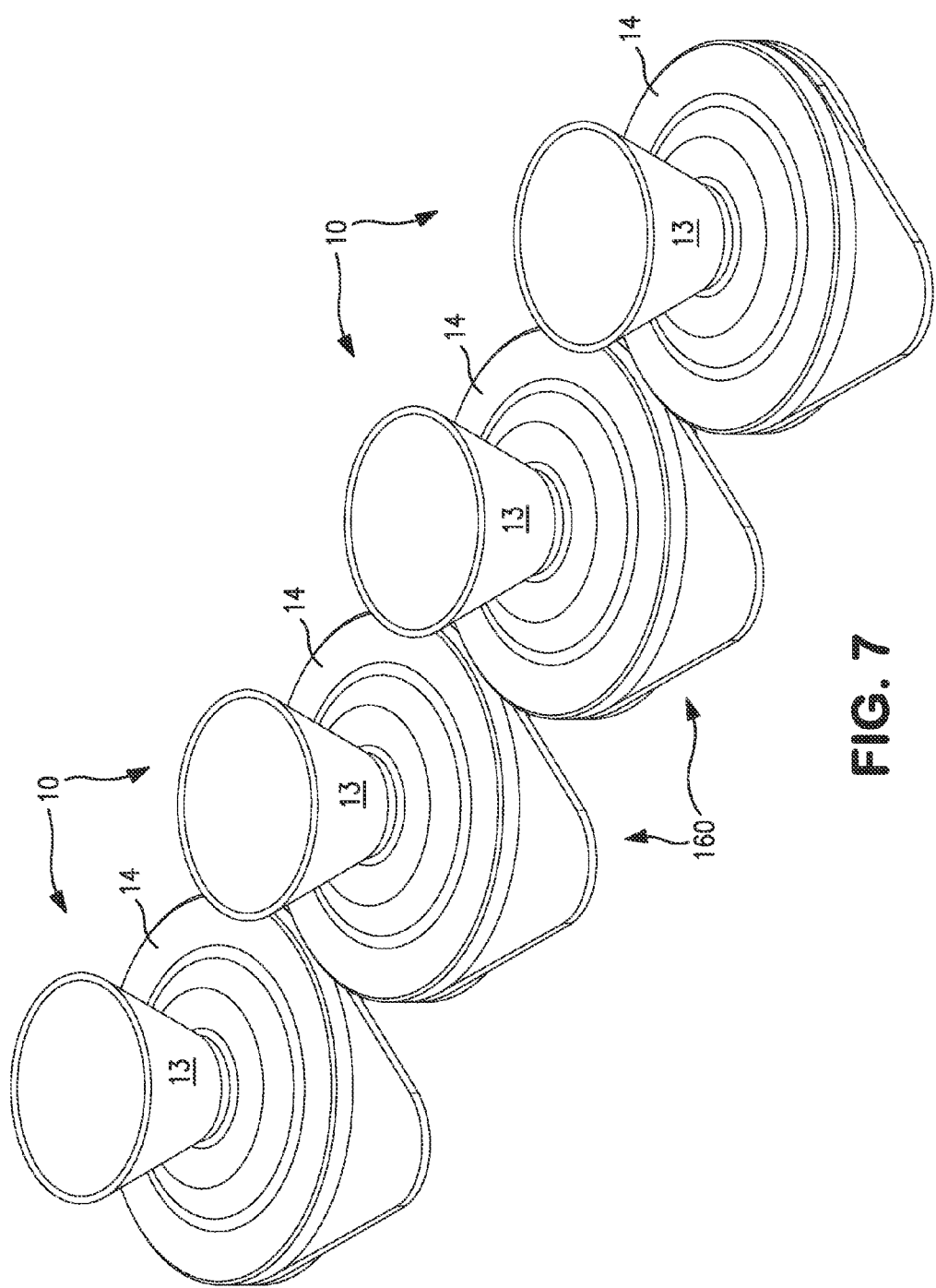
FIG. 7 is a perspective view of a plurality of interconnected filter assemblies in accordance with certain embodiments.
Figure 8:
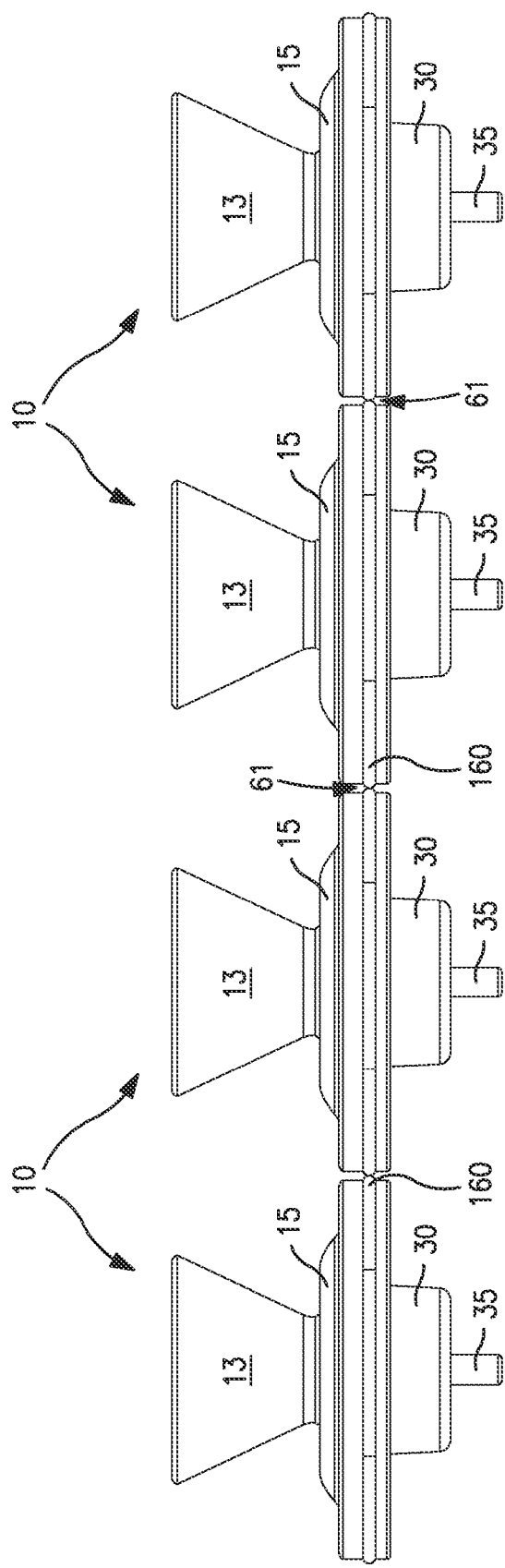
FIG. 8 is a side view of the plurality of filter assemblies of FIG. 7.
Figure 16:
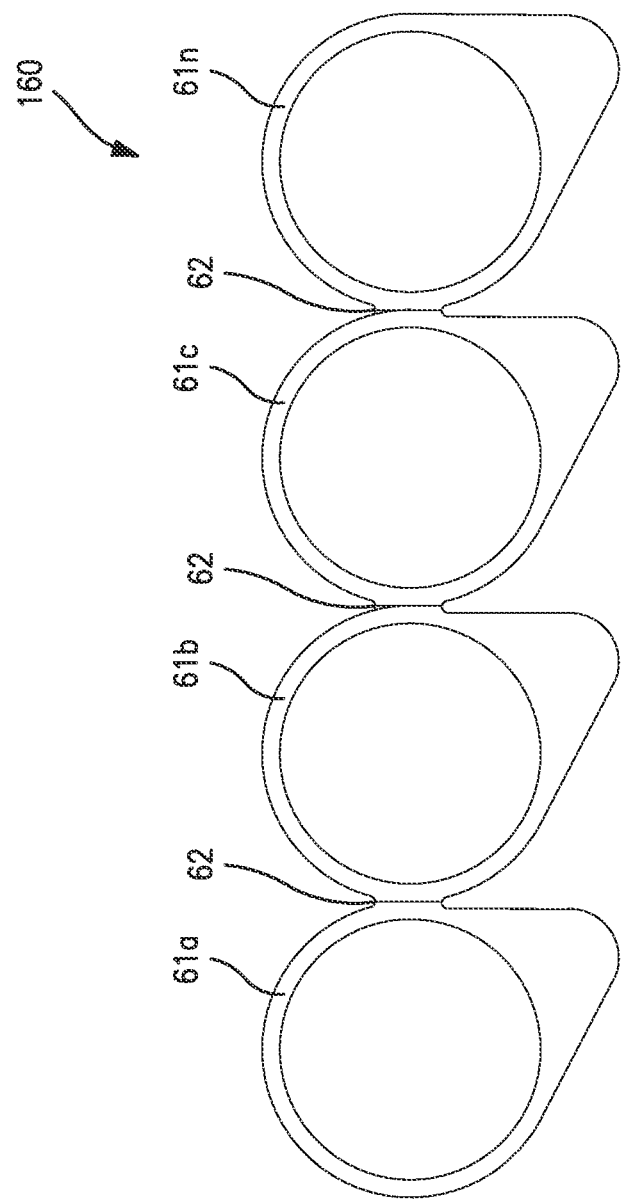
FIG. 16 is a top view of a connecting member in accordance with certain embodiments.

In certain embodiments, a plurality of filter assemblies 10 can be provided in integrated form. For example, an array of filter assemblies 10, such as four-member array shown in FIGS. 7 and 8, can be removably attached or conjoined in a linear array for ease of handling and use. In certain embodiments, a connecting member 160 (FIG. 16) is secured to each of the filter assemblies 10 in the array. For example, the connecting member 160 can include a plurality of annular rings 61a-61n, each having the same outside diameter as a base 14 and support member of a filter assembly 10, and can be positioned between the base 14 and support member 17 prior to affixing the base and support member together. One or both of the base 14 and support member 17 can include radially inward raised annular rings which help position the connecting member 160. Each adjacent annular ring can be removably affixed to the next annular ring, such as with perforations 62, so that flexing and/or tearing and/or snapping of the same repeatedly will cause the annular rings to separate from one another to disengage the interconnected array.

Figure 9:
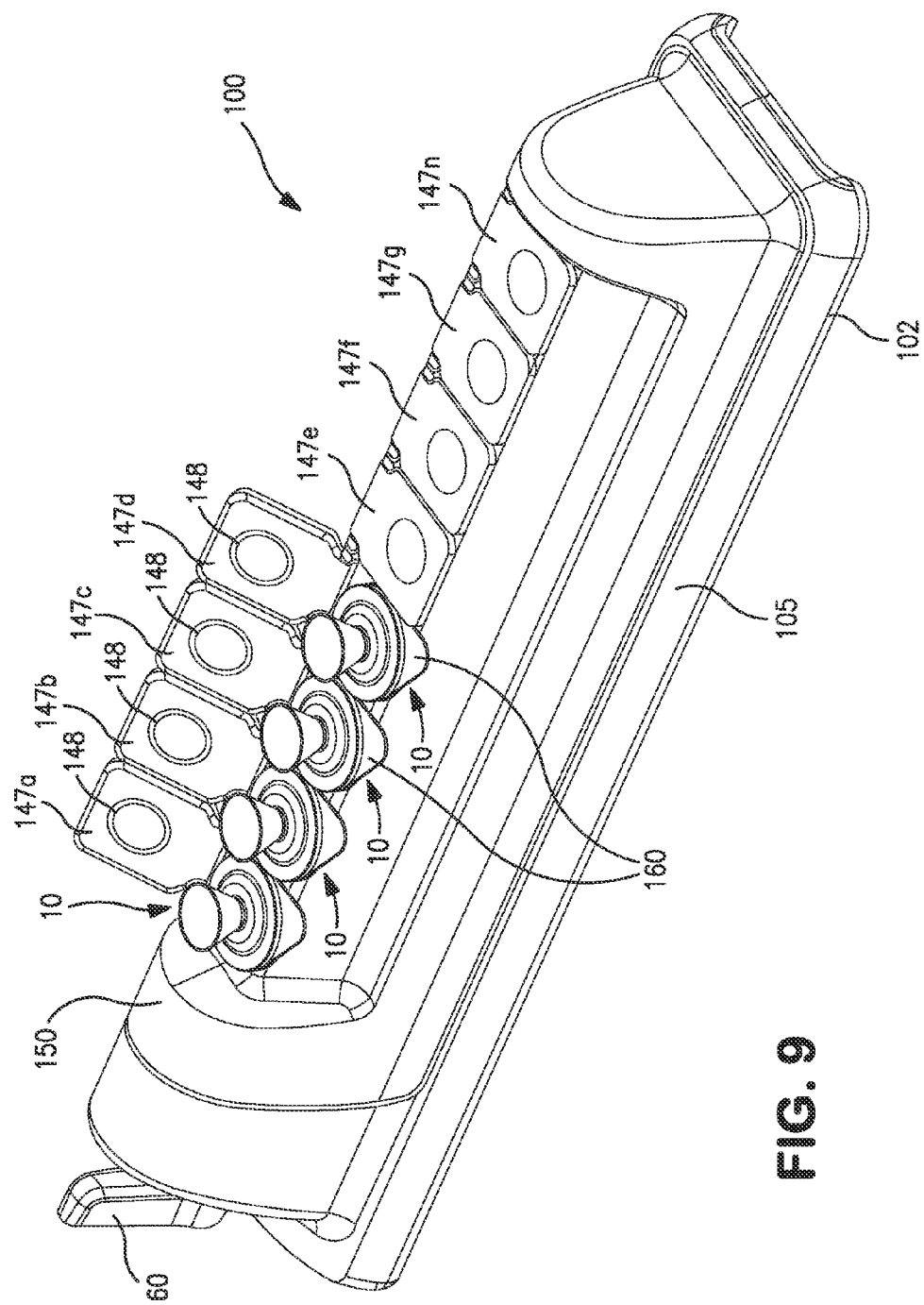
FIG. 9 is a perspective view of a sample preparation device with filters in accordance with certain embodiments.

Turning now to FIG. 9, there is shown a body 100 that in cooperation with filter assemblies 10, functions as a sample preparation device 100. The body 100 includes a base 102 having an elongated support member 105 for aligning and supporting a tray 110 for holding a sample container such as a vial. The support member 105 includes one or more apertures in fluid communication with a vacuum source via chamber 104. Preferably the base 102 is made of a plastic such as polypropylene, with an integrated seal member 120 made of a thermoplastic elastomer. The seal utilizes a "bead" feature to localize contact with the manifold lid around the perimeter of the vacuum manifold. This bead allows force applied by the user or resulting from a pressure differential to more effectively compress the seal and ensure conformity to the lid. Furthermore, the shape of the seal overall with its easily distinguishable left and right ends and arch shape helps to ensure correct placement of the lid upon the seal; the seal is thus "keyed" so that the lid can only be placed on the seal in one configuration. Preferably the seal is overmolded to the base, the bead being integral to the overmold. In accordance with certain embodiments, the material used for the seal should be sufficiently soft, such as a material having a Shore A durometer hardness of 25. Suitable materials include thermoplastic elastomers, with Teknor Apex Monprene® being particularly preferred in view of its chemical resistance properties. The seal should be sufficiently wide to ensure contact with the edge of the lid being sealed, but not too wide so as to force the seal to compress over a wide area. Widths of about ⅛ inch are suitable.

One or more alignment tabs 106, 107 can be positioned on the top surface of the elongated support member 105, the tab or tabs cooperating with a corresponding number of recesses in the vial tray 110 to properly align and position the vial tray on the body 100.

Figure 17:
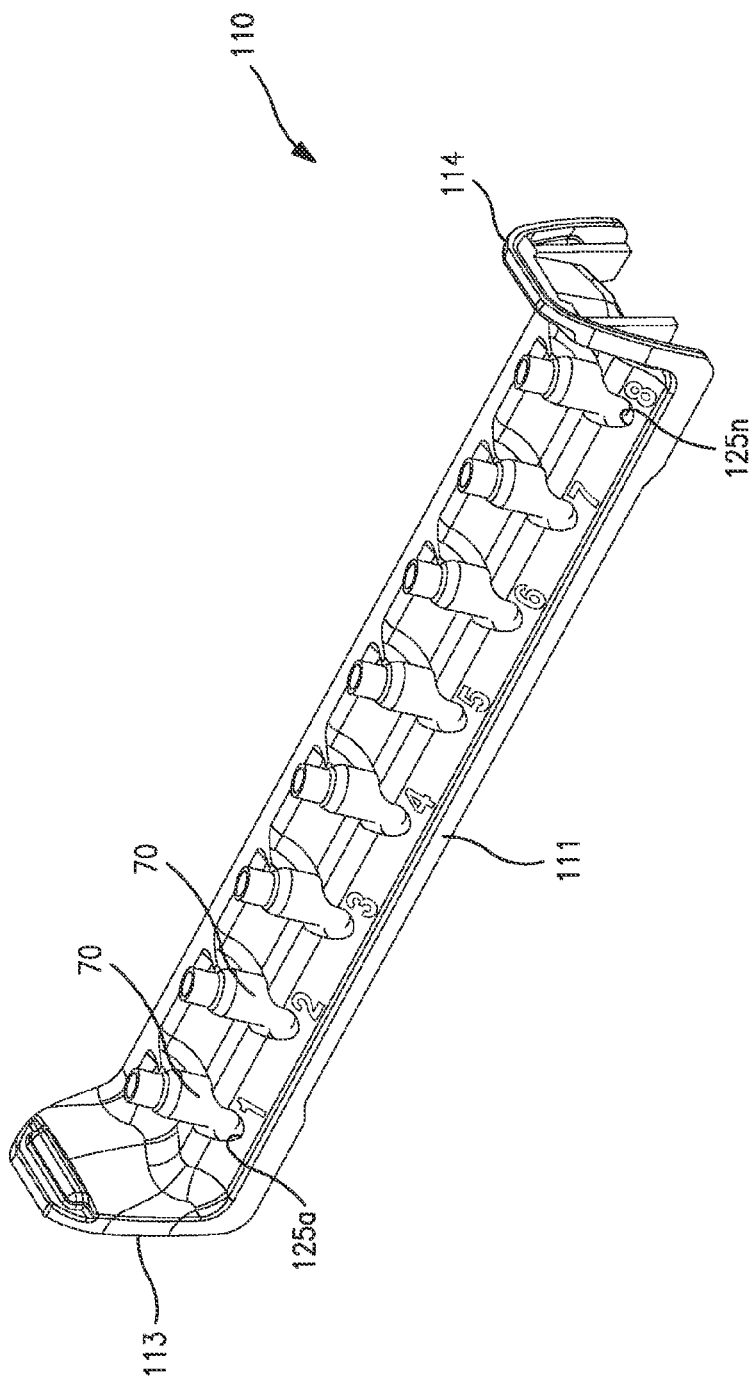
FIG. 17 is a perspective view of a container tray shown supporting a plurality of containers, in accordance with certain embodiments.
Figure 18:
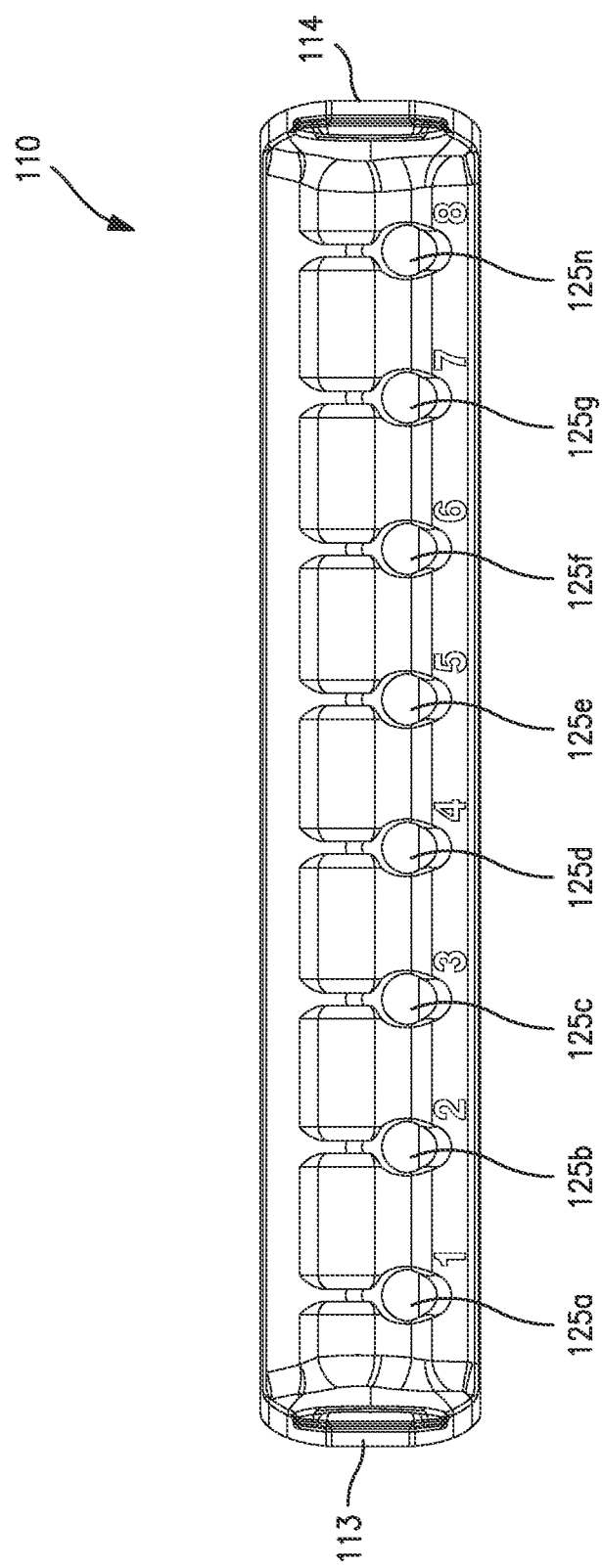
FIG. 18 is top view of a container tray in accordance with certain embodiments.
Figure 19:
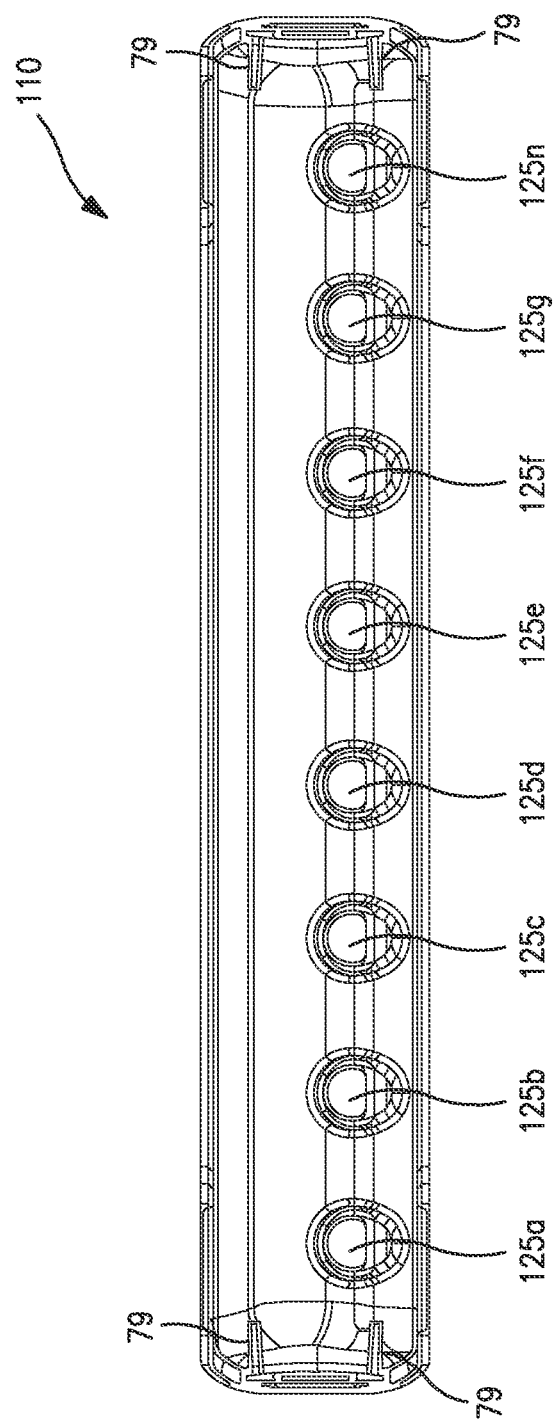
FIG. 19 is a bottom view of the container tray of FIG. 18.

In certain embodiments, the vial tray 110 is defined by an elongated base 111 and angled opposite side walls 113, 114. Preferably the angle of the side wall 113 matches the angle of wall 109 of the body 100. The vial tray includes a plurality of container receiving apertures 125a-125n (eight shown), creating vial receiving sockets. As seen in FIGS. 17 and 18, in certain embodiments the apertures are configured to receive and hold standard 12×32 mm vials, and are preferably angled. The angle is preferably such that the user has visibility of fluid flowing into the vials during filtration, and such that the fluid flows down the side wall of the vial to minimize or eliminate the trapping of air bubbles, and foaming, during vial filling. The angle ensures that the vials are located at a suitable location relative to the filter tip. The angle also facilitates access of the vials to the user, enabling the user to grasp each vial with their fingers while the vial remains in the tray, and attach or remove a vial cap (such as by screwing the cap onto the vial or off of the vial) while the vial remains in the tray. Thus, the shape of the vial receiving sockets uses this angle to rest each vial on deep and tall geometry behind the vial, with a minimum height wrapping around the front. The support, coupled with this "lean-back" angle, is sufficient to prevent loss of vials from all but the most extreme tipping of the tray, but does not interfere with viewability or access to the vials. One suitable angle is about 20° off of vertical. Each aperture can be numbered or otherwise marked to identify each individual container supported therein. The vial tray 110 is readily removable from the vacuum chamber, and thus can be used as a storage tray for the vials separately from the sample preparation device. Spaced stacking feet 79 may be provided on the underside of the tray 110 as shown in FIG. 19.

Figure 11:
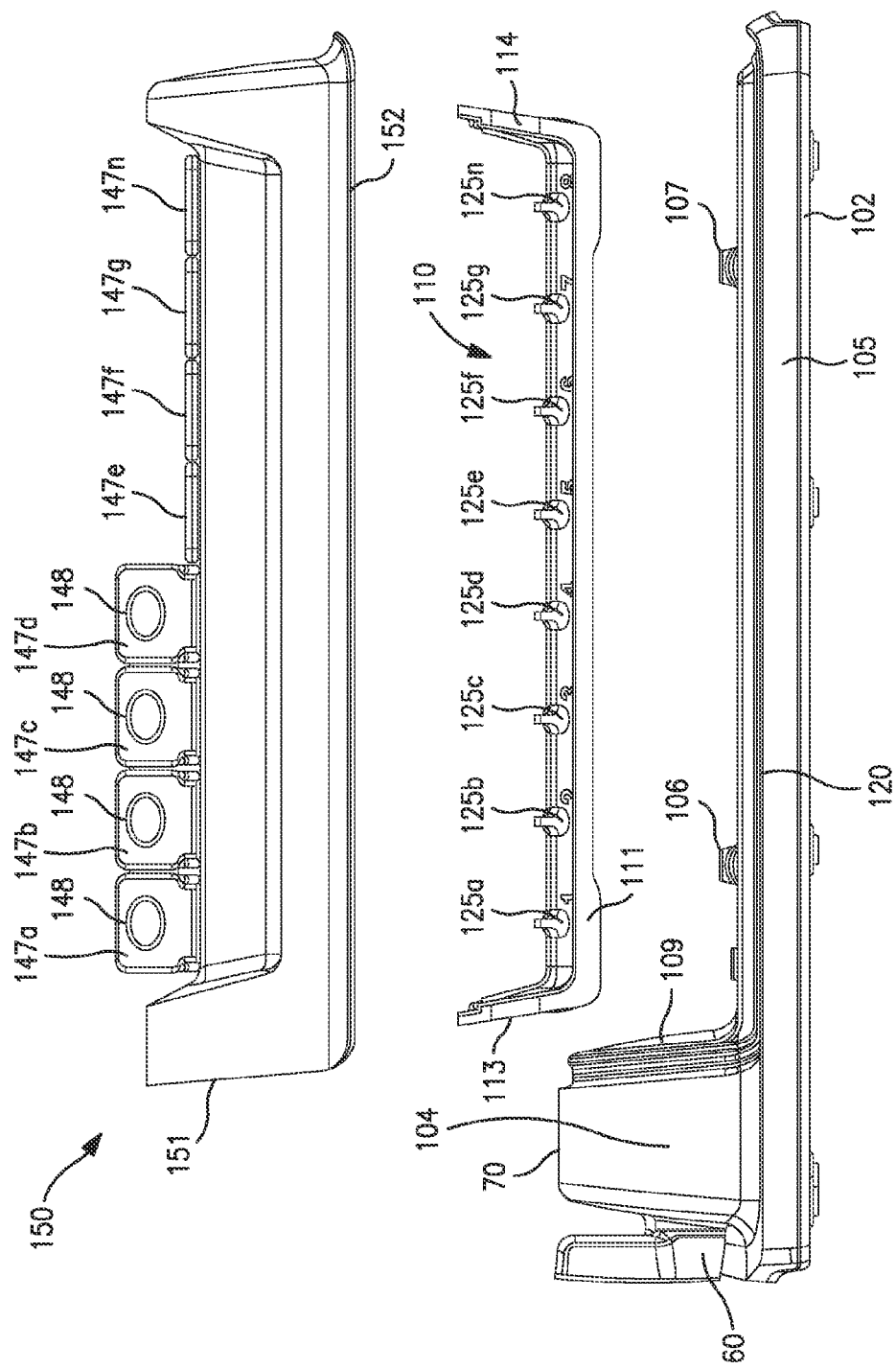
FIG. 11 is an exploded view of the device in accordance with certain embodiments.
Figure 12:
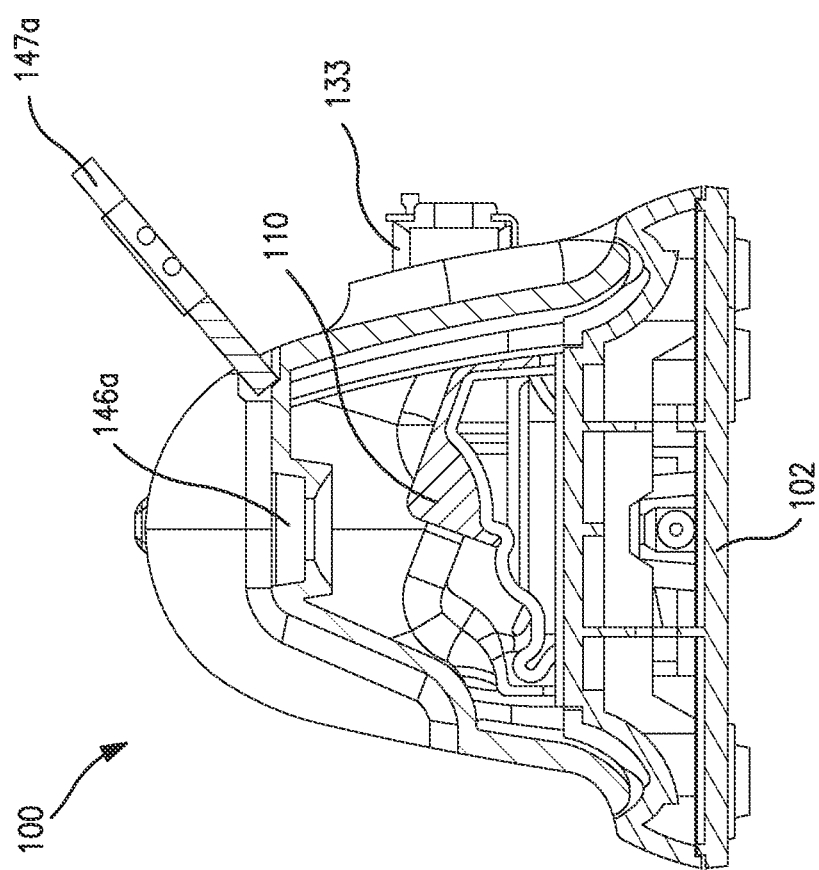
FIG. 12 is an end view, in cross-section, of the device in accordance with certain embodiments.
Figure 14:
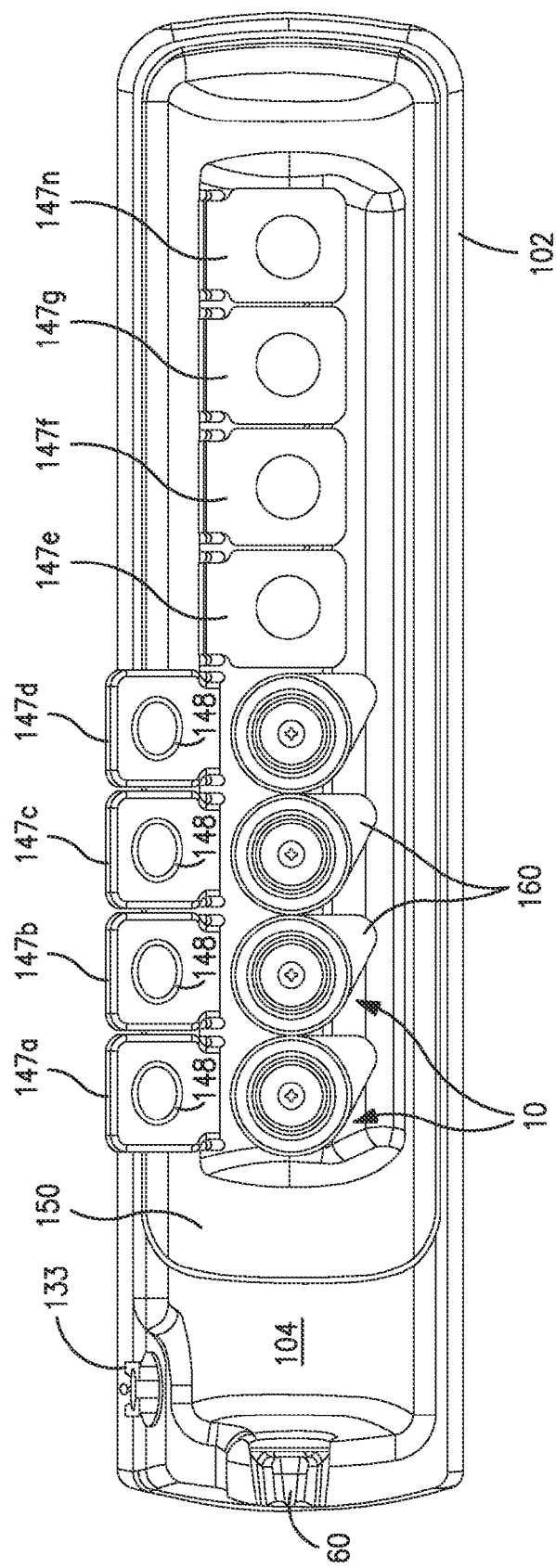
FIG. 14 is a top view of a sample preparation device with filter assemblies in place in accordance with certain embodiments.
Figure 20:
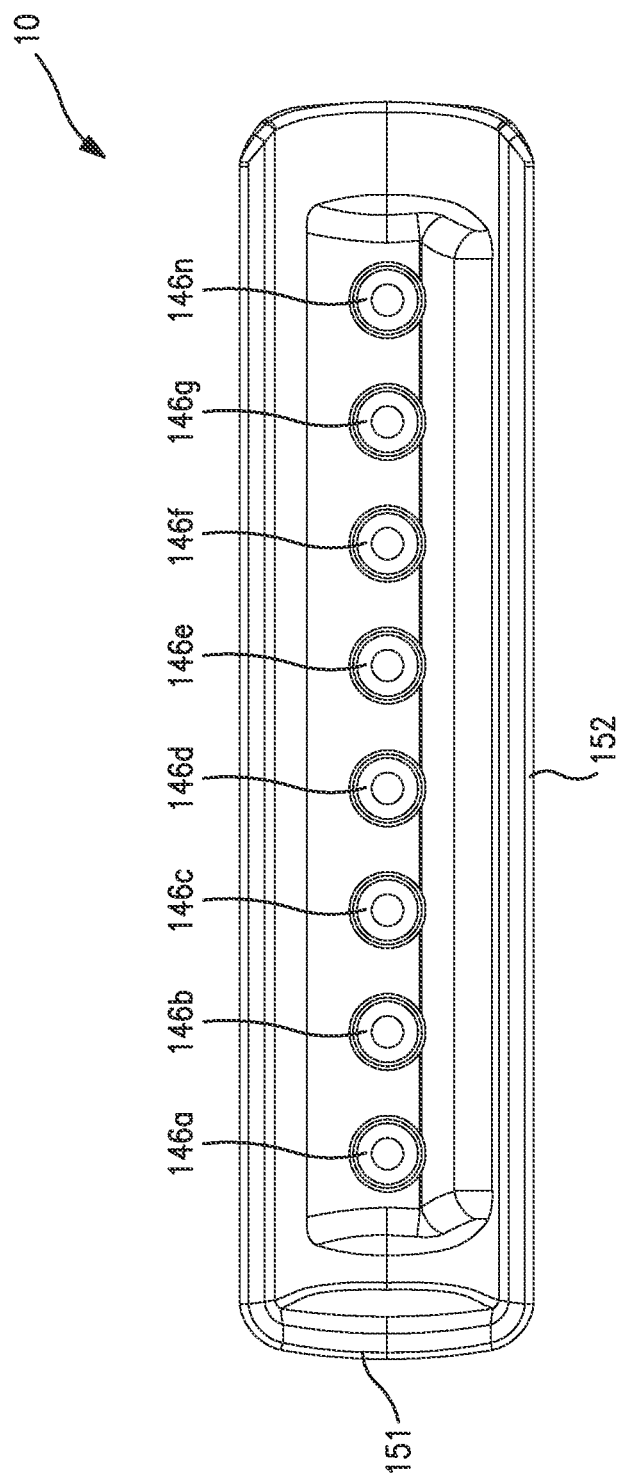
FIG. 20 is a bottom view of lid in accordance with certain embodiments.
Figure 21:
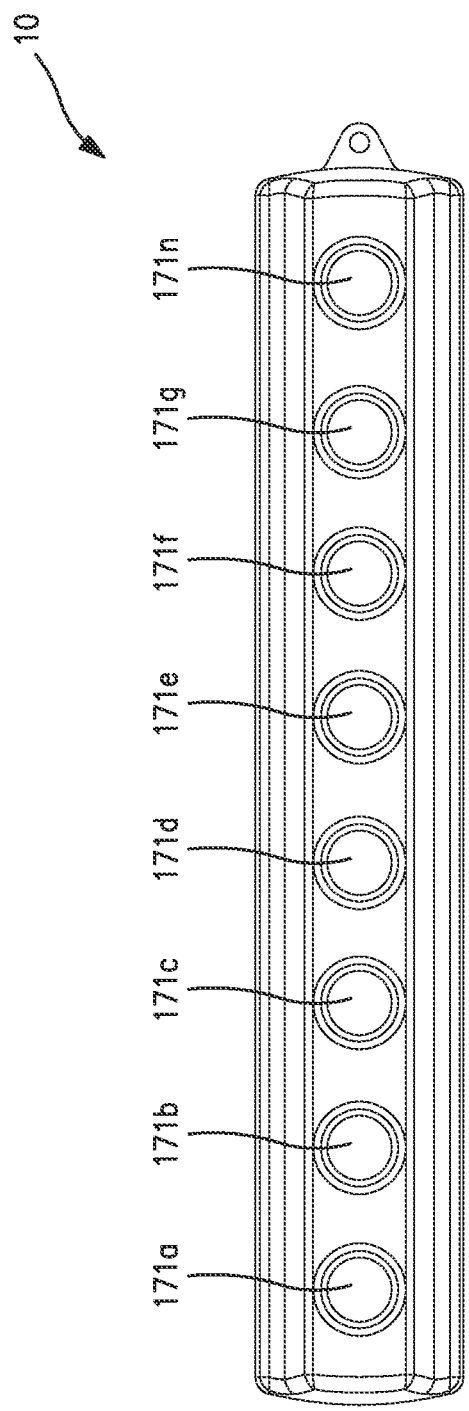
FIG. 21 is a top view of the waste collection tray in accordance with certain embodiments.
Figure 22:
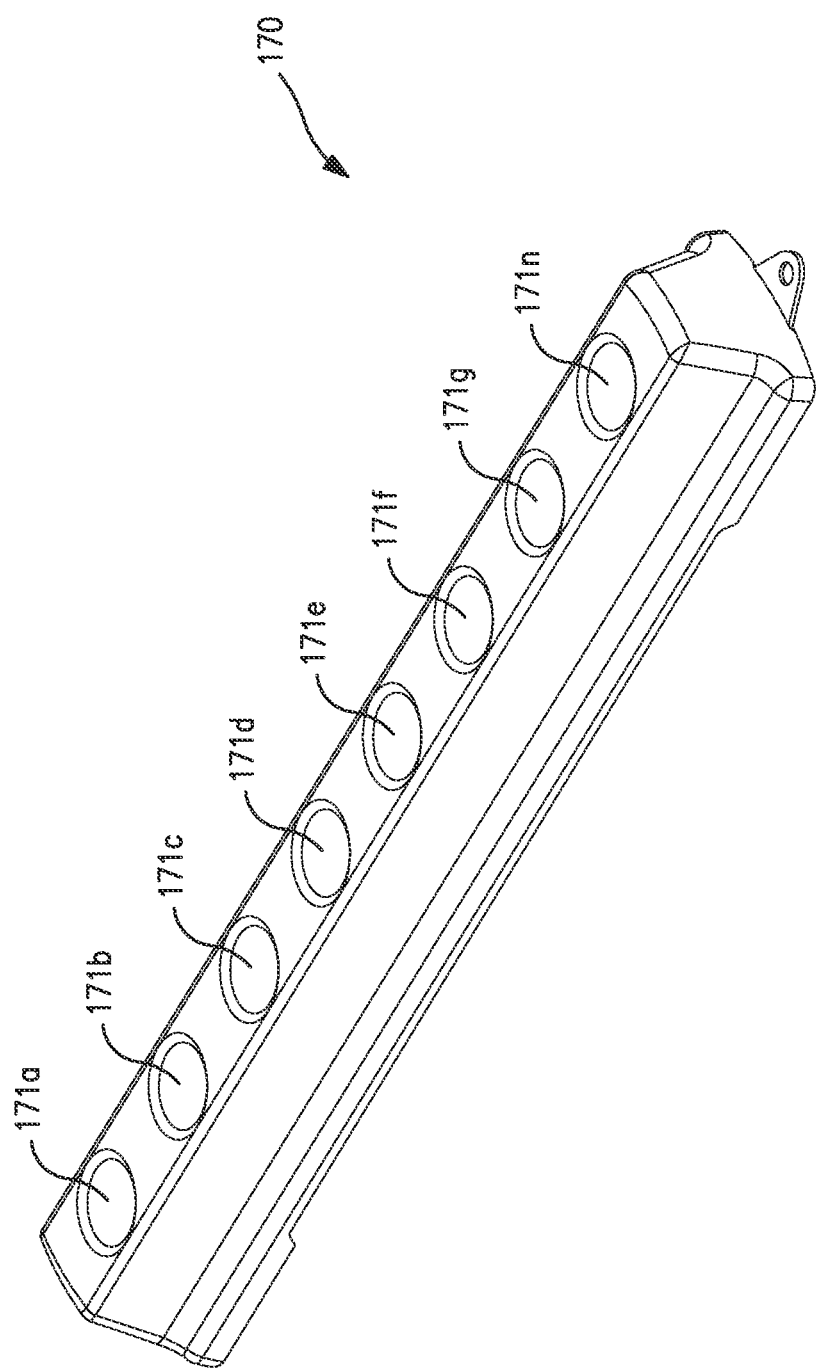
FIG. 22 is a perspective view of the waste collection tray.
Figure 23:
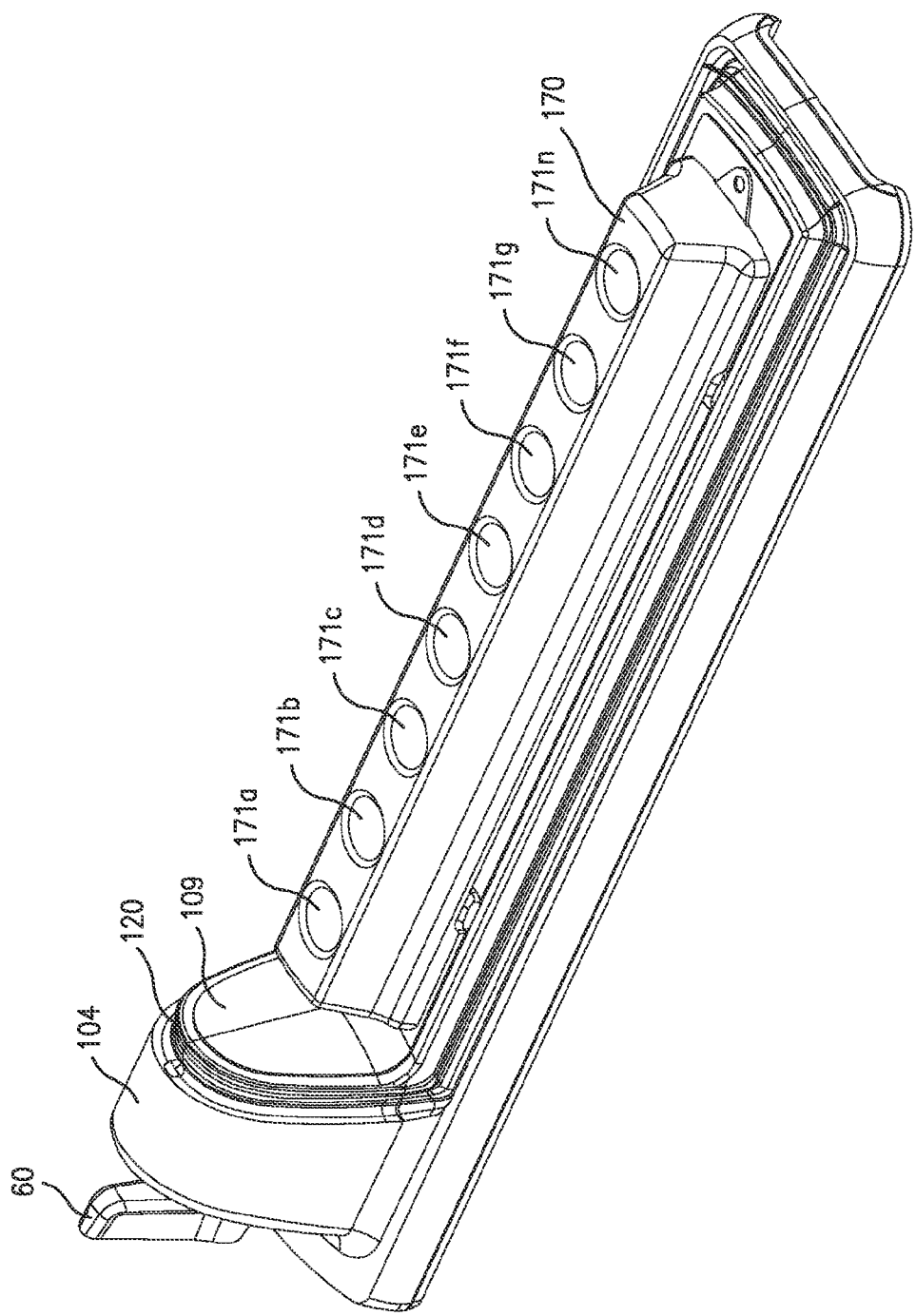
FIG. 23 is a perspective view of a sample preparation device including a waste collection tray in accordance with certain embodiments.

As seen in FIGS. 11 and 14, the sample preparation device 100 also includes a removable lid 150. In certain embodiments, the transverse cross-sectional shape of the lid 150 is parabolic, matching the shape of the perimeter of wall 109 and the seal member 120 along wall 109. Preferably the wall 109 and seal thereon are recessed downwardly from the top wall 70 of the chamber 104 (FIG. 11), providing a shoulder for receiving the edge of the lid 150. Accordingly, lid 150 fits over the seal member 120 along the inner perimeter (FIG. 20) of the parabolic side wall 151, and along the underside 152 of the elongated base portion 152. Upon the application of vacuum, the lid 150 thus seals to the member 105 along the lid perimeter, thereby defining a vacuum chamber between the lid and the base. Preferably the lid 150 is made of a clear or transparent material, such as an polymethylpentene, which is chemically resistant and allows the user to observe the filtration process as it proceeds, and obtain visual feedback that filtration is complete and that sample properly transferred into the vial, for example.

Figure 10:
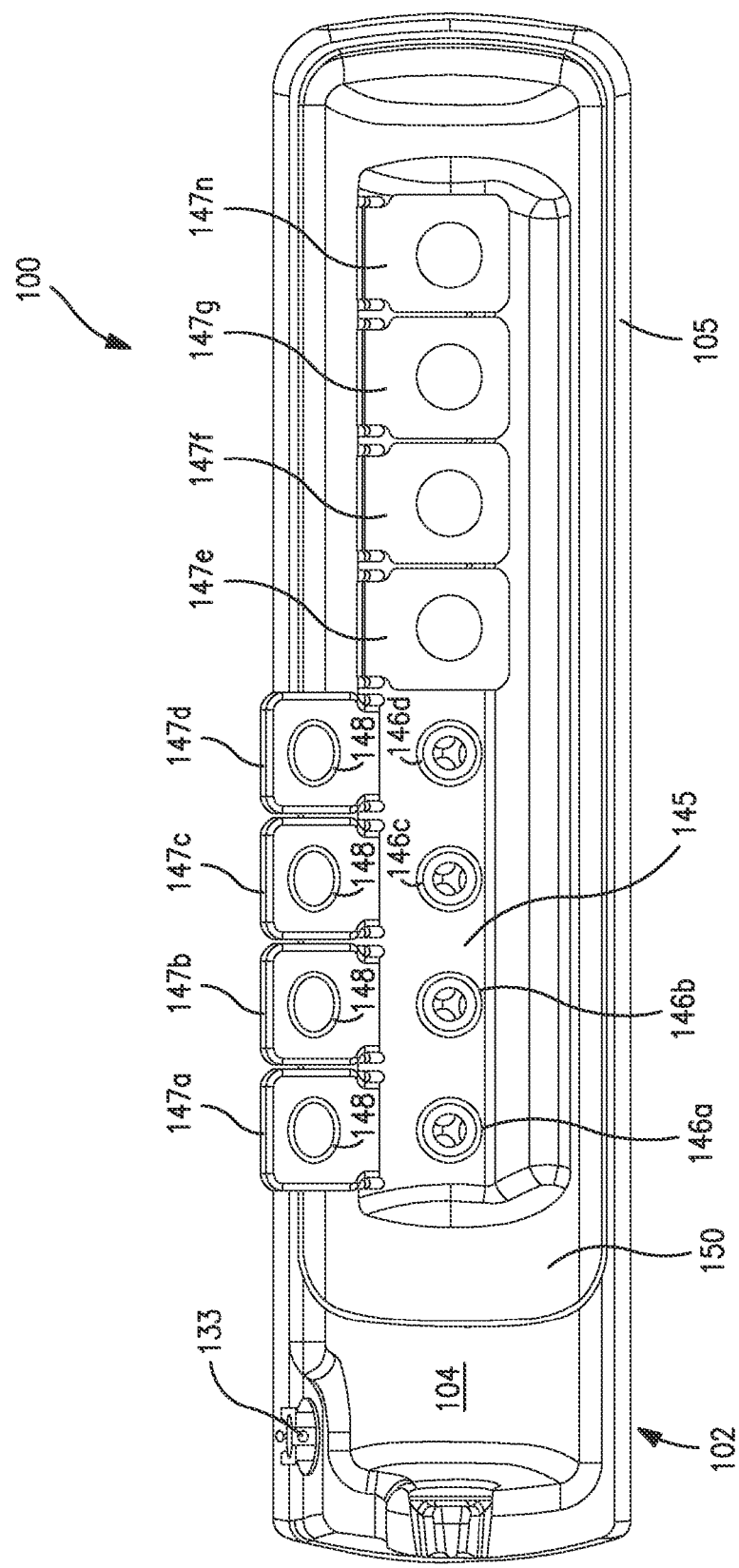
FIG. 10 is a top view of the device of FIG. 9 (without filters in place)

The lid 150 includes an elongated recessed top surface 145 (FIG. 10), which includes at least one, preferably a plurality, of spaced apertures 146a-146n. The apertures 146a-146n are each configured to receive in sealing relation a collar member 30 of a respective filter assembly 10. Accordingly, where a plurality of apertures are present, the apertures 146a-146n are spaced a sufficient distance from each other to accommodate a filter assembly 10 sealingly arranged in each. Four such filter assemblies 10 are shown so arranged in FIG. 9. Each aperture in the lid 150 also may be associated with a corresponding sealing member, such as an individual plug that can be removable, or more preferably a door 147a-147n, each of which is preferably pivotable on the lid 150 between a closed position (e.g., door 147e in FIG. 9) in which it seals against its respective aperture, and an open position (e.g., door 147a in FIG. 9) in which the respective aperture is accessible for sealing engagement with a filter assembly 10. The underside of each door preferably includes a raised annular ring 148 that sealingly engages in or about the perimeter of its corresponding aperture on the lid 150 when the door is in the closed position. Each door allows the aperture it is associated with to be sealed in the event that aperture is not being used to filter a sample. This allows the device to be used to filter any number of samples simultaneously, depending upon the number of apertures present (eight in the embodiment illustrated).

The body 100 includes chamber 104 which houses a valve for turning the vacuum on or off. For example, as seen in FIGS. 24-27, a ball valve 155 (e.g., a two-way, right angle ball valve) is housed in valve cradle 144 in the chamber 104. The ball valve can be actuated (e.g., by pivoting handle 60) between an open position, in which fluid communication with a vacuum source via connector 133 is realized, and a closed position in which fluid communication with a vacuum source is shut off. Alternatively, the valve can be controlled by other means known to those skilled in the art, such as electrically or pneumatically. The chamber 104 is connectible to a vacuum source via integrated connector 133, which provides fluid communication via a hose or the like (not shown), between the chamber 104 and the vacuum source, and thus pulls a vacuum, via the one or more apertures in member 105, in the vacuum chamber region below the lid 150. For example, tubing 148 is connected, through the valve 155, to the vacuum source. A T-fitting 149 is provided in the tubing line, which provides a orifice 141 communicating with the vacuum chamber. The opposite end of the tubing 148 from the connection to the valve 155 is connected to an orifice fitting 143 to vent.

Turning now to FIGS. 20-23, a waste collection tray 170 can be provided and used in place of the vial tray 110 if filtration to waste is desired. The waste collection tray 170 can have a plurality of wells 171a-171n (eight shown), with each well being aligned with a respective aperture 146 when the waste collection tray 170 is positioned in the vacuum chamber as per FIG. 23.

In operation, the vial tray 110 is placed in the device and positioned properly using the alignment tabs 106, 107. One or more sample containers 70 such as vials are inserted into respective apertures 125a-125n depending upon the number of samples to be filtered. The lid 150 is then placed over the vial tray 110, thereby enclosing the vacuum chamber which includes the vial tray 110 and any vials contained therein. One or more filter assemblies 10 are each placed in a respective aperture 146a-146n, again depending upon the number of samples to be filtered. The remaining apertures are sealed by ensuring that the corresponding door 147 associated therewith is in the closed position. When a filter assembly 10 is disposed in an aperture 146 and a corresponding vial is disposed in the vial tray 110, a portion of the stem 35 is nested within the vial (FIG. 13), thereby reducing or eliminating any cross-contamination between that filter assembly 10 and a different vial, and reducing or eliminating any fluid spillage during transfer from the filter assembly 10 to the vial. Sample is introduced into each of the sample reservoirs 12. The connector 133 is attached to a vacuum source such as with a quick disconnect and suitable hosing, and the vacuum source is turned on (e.g., 25 in Hg). The handle 60 is actuated, placing the manifold in fluid communication with the vacuum, which seals the lid 150 and the body 100 together. The vacuum drives the filtration in each of the filtration assemblies 10 simultaneously and in parallel, and the sample from each filter assembly is driven through the membrane, into and through the bore 36 of elongated tip 35, and directly into a corresponding unique vial with no cross-contamination. The vials may then be capped and removed from the tray, or may remain in the tray and the tray removed from the vacuum chamber and stored elsewhere, such as under refrigeration. The filtered sample in the vials may undergo further processing, such as liquid chromatography.

What is claimed is:

1. A sample preparation device for preparing one or more samples, comprising:

at least one filter assembly; and
a body comprising a base, a sample container tray for holding one or more sample containers, and a lid, said lid being mounted on said base in sealing relation with said base and defining with said base a vacuum chamber, said lid having one or more apertures in each of which a respective one of said at least one filter assemblies is sealingly engaged; wherein said base has a thermoplastic elastomer seal that is keyed so that said lid can be sealed to said base in only one configuration.

2. The sample preparation device of claim 1, wherein said lid comprises a plurality of said apertures and a sealing member associated with each said aperture, each said sealing member being movable between an open position in which the associated aperture is accessible for sealing engagement with a filter assembly, and a closed position in which the associated aperture is not accessible for sealing engagement with a filter assembly.

3. The sample preparation device of claim 2, wherein said closed position seals said aperture.

4. The sample preparation device of claim 1, wherein said lid is removable from said base to provide access to said sample container tray.

5. The sample preparation device of claim 1, wherein said lid comprises a plurality of said apertures, each having a filter assembly disposed therein in sealing relation, and a plurality of sample containers are disposed in said sample container tray, and wherein each of said filter assemblies aligns with a respective one of said sample containers and is in fluid communication therewith.

6. The sample preparation device of claim 1, wherein said at least one filter assembly comprises a sample reservoir in fluid communication with porous media; an axially extending collar member configured to engage with one of said one or more apertures in sealing relation; and an elongated tip having a bore in fluid communication with said sample reservoir.

7. The sample preparation device of claim 6, further comprising at least one sample container disposed in said sample container tray, and wherein said elongated tip of said filter assembly is nested in said at least one sample container.

8. The sample preparation device of claim 1, wherein said filter assembly comprises a collar member configured to seal in one of said apertures of said lid.

9. The sample preparation device of claim 1, wherein said lid comprises transparent material.

10. The sample preparation device of claim 1, further comprising a waste tray.

11. The sample preparation device of claim 1, wherein said at least one filter assembly comprises an axially extending member positioned to nest in a respective one of said one or more sample containers.

12. The sample preparation device of claim 1, wherein said at least one filter assembly filters said sample and produces filtrate, and wherein one or more sample containers is positioned in said sample container tray such that the level of said filtrate flowing from said at least one filter assembly to a respective sample container can be determined visually without removing said sample container from said sample container tray.

13. The sample preparation device of claim 1, wherein there are a plurality of sample containers, each separate from a filter assembly.

14. The sample preparation device of claim 1, wherein said seal is overmolded to said base.

* * * * *